US005653986A

United States Patent [19]

Morris, Jr. et al.

[11] Patent Number: 5,653,986

[45] Date of Patent: Aug. 5, 1997

[54] *VIBRIO CHOLERAE* BENGAL SEROGROUP-O139 CAPSULAR POLYSACCHARIDE AND PROTEIN CONJUGATES THEREOF

[75] Inventors: J. Glenn Morris, Jr., Baltimore; Judith A. Johnson, Catonsville; C. Allen Bush, Baltimore, all of Md.

[73] Assignee: University of Maryland at Baltimore, Baltimore, Md.

[21] Appl. No.: 465,905

[22] Filed: Jun. 6, 1995

Related U.S. Application Data

[63] Continuation of Ser. No. 159,503, Nov. 30, 1993, abandoned.

[51] Int. Cl.$^6$ .......................... A61K 39/106; A61K 39/00; A61K 39/385; C07H 3/06

[52] U.S. Cl. .......................... 424/261.1; 424/184.1; 424/193.1; 424/197.11; 536/1.11

[58] Field of Search .......................... 424/261.1, 184.1, 424/193.1, 197.1; 536/1.1

[56] References Cited

PUBLICATIONS

Shimizu et al, "Biological Activities of Lipopolysaccharide Isolated from *Vibro cholerae* O139, a New Epidemic Strain for Recent Cholera in Indian Subcontinent", *Microbiol. Immunol.*, 38(6):471–474 (1994).

Panigrahi et al, "Human Immune Response to Non–01 *Vibrio cholerae* Serotype O139", Abstract, 95th General Meeting, Washington, D.C.

Comstock et al, "Cloning of a Region Associated with Capsule and O Antigen Expression of *Vibrio cholera* Serogroup O139", Abstract, 95th General Meeting, Washington, D.C.

Johnson et al, "Recognition of Pathogenic Strains of *Vibrio Cholerae* with Restriction Fragments Containing Ribosomal RNA Operon Sequences", Abstract, ASM 1995.

Comstock et al, "The Capsule and O Antigen in *Vibrio cholera* O139 Bengal Are Associated with a Genetic Region Not Present in *Vibrio cholerae* O1", *Infect. Immun.*, 63(1):317–323 (1995).

Morris, Jr. et al, "*Vibrio cholerae* O139 Bengal," *In: Vibro Cholea* and *Cholera*, Ed., Wachsmuth et al, AMS Press, Washington, D.C., Chapter 7, pp. 95–102 (1994).

Morris et al, The Journal of Infectious Disease 171:903–8, 1995, Clinical & Immunologic Characteristics in *Vibrio cholerae* O139 Bengal Infection in N.A. volunteers.

Adams et al The Journ of Clin. Microbiology 19:181–186–1984.

Kabir et al (2) J Med. Microbiol 23:9–18, 1987.

Raziuddin et al Infect & Immun 27:211–215 1980.

Johnson et al Infect & Immunity 60:864–869 1992.

Kabir et al Infect & Immun 38:1263–1272, 1982.

Jann et al Eur J. Biochem 37:531–534, 1973.

Gupta et al Infection & Immun. 60:3201–3208, 1992.

Dick et al. Contribution to Microbiology & Immunology 10:48–114 1989.

Hisatsune et al Biochem Biophys. Res. Com 196:1309–1315, 1993.

Johnson et al, "Non–O1 *Vibro cholerae* NRT36S Produces a Polysaccharide Capsule That Determines Colony Morphology, Serum Resistance, and Virulence in Mice", *Infect. Immun.*, 60(3):864–869 (Mar., 1992).

Johnson et al, "Characterization of Non–O1 *Vibro cholerae* Strains from the Bangladesh Epidemic", *33rd Interscience Conference on Antimicrobial Agents and Chemotherapy*, Abstract and Poster Presentation, New Orleans, Lousiana (Oct. 17–20, 1993).

Watson et al, "Protection of Mice Against *Salmonella typhimurium* with an O–Specific Polysaccharide–Protein Conjugate Vaccine", *Infect. Immun.*, 60(11):4679–4686 (Nov., 1992).

Wenger et al, "Efficacy of *Haemophilus influenzae* Type B Polysaccharide–Diphtheria Toxiod Conjugate Vaccine in US Children aged 18–59 months", *The Lancet*, 338(8764):395–398 (Aug. 17, 1991).

Johnson et al, "Non–O1 *Vibrio cholerae* (O39 Synom. Bengal) from the India/Bangladesh Epidemic are Encapsulated", *29th Joint Conference on the U.S.–Japan Cooperative Medical Science Program–Cholera and Related Diahreal Diseases,* Monterrey, California (Dec. 1993).

Devi et al, "Antibodies to Poly [(2→8)α–N–acetylneuraminic acid] and Poly [(2→9)–α–N–acetylneuraminic acid] are Elicited by Immunization of Mice with *Escherichia coli* K92 Conjugates: Potential Vaccines for Groups B and C Meningococci and *E. coli* K1", *Proc. Natl. Acad. Sci. USA*, 88:7175–7179 (Aug., 1991).

*Primary Examiner*—Hazel F. Sidberry

*Attorney, Agent, or Firm*—Sughrue, Mion, Zinn, Macpeak & Seas

[57] ABSTRACT

Substantially pure capsular polysaccharide obtained from *Vibrio cholerae* Bengal serogroup-O139, capsular polysaccharide-protein conjugates thereof, and antibodies having binding specificity to said capsular polysaccharide.

4 Claims, 3 Drawing Sheets

*VIBRIO CHOLERAE* BENGAL SEROGROUP-O139 CAPSULAR POLYSACCHARIDE AND PROTEIN CONJUGATES THEREOF

This application is a continuation of application Ser. No. 08/159,503 filed Nov. 30, 1993, now abandoned.

The development of the present invention was supported by the University of Maryland, and the U.S. Department of Veterans Affairs.

FIELD OF THE INVENTION

The present invention relates to substantially pure capsular polysaccharide obtained from *Vibrio cholerae* Bengal serogroup-O139, capsular polysaccharide-protein conjugates thereof, and antibodies having binding specificity to said capsular polysaccharide.

BACKGROUND OF THE INVENTION

*Vibrio cholerae* (*V. cholerae*) of O group 1 cause the disease cholera, a well-recognized cause of morbidity and mortality throughout the world. To date, there have been seven recorded pandemics of this severe dehydrating diarrheal disease (Barua et al, Eds., *Cholera*, pgs. 1–36, Plenum Medical Book Company, New York (1992)). Diarrhea caused by *V. cholerae*O1 is due to the action of cholera toxin. Mortality without medical treatment can be as high as 70% (Barua et al, supra).

*V. cholerae* of O groups other than 1 (non-O1, or non-agglutinating (NAG) *V. cholerae*) also cause gastrointestinal disease (Spitell et al, Eds., *Clinical Medicine*, Harper and Row, Philadelphia (1991)); and Morris et al, Epidemiol. Rev., 12:179–191 (1990)), as well as extraintestinal infections, such as wound infections and septicemia (Morris et al, supra; and Safrin et al, *Rev. Infect. Dis.*, 10:1012–1017 (1987)).

Until recently, it was believed that only O1 strains have epidemic potential, with non-O1 strains being limited to sporadic cases and small outbreaks. However, in late 1992 a large outbreak of severe cholera-like disease started in Eastern India (Albert et al, *Lancet*, 341:704 (1993); Ramamurthy et al, *Lancet*, 341:703–704 (1993); Jesudason et al, *Lancet*, 341:1090 (1993); and Albert et al, *Lancet*, 342:387–390 (1993)), and spread to Bangladesh in January 1993 (Chongsa-nguan et al, *Lancet*, 342:430–431 (1993)). By April, 1993, more than 15,000 people had been affected, and at least 700 had died from this epidemic (Ramamurthy et al, supra; and Chongsa-nguan et al, supra). Only non-O1 *V. cholerae* were isolated from a majority of the patients. These isolates have since been typed and designated O139 synom. Bengal.

The current epidemic is spreading rapidly, and *V. cholerae* O139 Bengal is replacing *V. cholerae* O1 in affected areas (Chongsa-nguan et al, supra). Tracking the spread of the epidemic requires a means of determining whether persons have been exposed to this new strain of *V. cholerae*. Further, correct diagnosis of infected persons, and effective public health interventions will depend on an effective means of rapidly identifying the causative agent in environmental or clinical samples.

Previous exposure to *V. cholerae* can be determined by testing serum samples for specific antibodies induced by the infection. During O1 *V. cholerae* infection, antibodies against a variety of antigens are induced, with lipopolysaccharide (LPS) and cholera toxin (CT) eliciting the highest titers (Levine et al, *Microbiol. Rev.*, 47:510–560 (1983); and Kaper, *Rev. Infect. Dis*, 11:S568–S573 (1989)). While *V. cholerae* O1 and *V. cholerae* O139 Bengal have been found to be very closely related phylogenetically, and share many antigens, including CT, there are antigenic differences in the LPS (Albert at al, supra; Ramamurthy et al, supra; and Jesudason et al, supra). It has been found that *V. cholerae* O139 Bengal LPS is truncated. Therefore, there may be problems with immunogenicity of the O139 Bengal LPS, as well as cross-reactivity with O1 LPS. Accordingly, there is a need to find and provide additional antigens which are specific for *V. cholerae* O139 Bengal infection, and which can be identified quickly and easily.

In contrast to *V. cholerae* O1, it was found in the present invention that *V. cholerae* O139 Bengal produces a polysaccharide capsule. This was an unexpected finding for a strain causing epidemic cholera, as *V. cholerae* O1 are not encapsulated. That is, capsules have previously been seen only on non-epidemic strains of *V. cholerae*. Further, in contrast to *V. cholerae* O139 Bengal, these non-epidemic strains generally do not produce CT, and, in the past, have only been associated with sporadic illness. Thus, the discovery and purification of the capsular polysaccharide of *V. cholerae* O139 Bengal in the present invention provides, for the first time, the ability to quickly and easily identify O139 Bengal infection.

Moreover, the age distribution of the current O139 Bengal epidemic indicates that previous infection with O1 strains of cholera does not induce protective immunity against the new strain. Therefore, cholera vaccines currently being developed against *V. cholerae* O1 will not be effective against the new threat caused by *V. cholerae* O139 Bengal (Chongsa-nguan et al, supra; and Albert et al, supra). Thus, the discovery and purification of the capsular polysaccharide of *V. cholerae* O139 Bengal in the present invention provides, for the first time, the ability to produce vaccines effective against O139 Bengal infection.

SUMMARY OF THE INVENTION

Accordingly, an object of the present invention to provide a substantially pure *V. cholerae* O139 Bengal antigen, as well as a method for detecting and identifying *V. cholerae* O139 Bengal grown from an unknown sample, particularly an unknown sample from a human or animal, or from an environmental sample, using said antigen.

Another object of the present invention is to provide antibodies that are specific for *V. cholerae* O139 Bengal, as well as a method for detecting and identifying *V. cholerae* O139 Bengal grown from an unknown sample, particularly an unknown sample from a human or animal, or from an environmental sample, using said antibodies.

A further object of the present invention is to provide a capsular polysaccharide-protein conjugate that is capable of inducing *V. cholerae* O139 Bengal capsule specific antibodies.

Yet another object of the present invention is to provide a vaccine effective against *V. cholerae* O139 Bengal infection containing said conjugate, as well a method for treating said infection employing such a vaccine.

These and other objects of the present invention, which will be apparent from the detailed description of the invention provided below, have been met, in one embodiment, by substantially pure *V. cholerae* O139 Bengal capsular polysaccharide, and the use of the same to detect and identify *V. cholerae* O139 Bengal infection.

In another embodiment, the above-described objects of the present invention have been met by antibodies having binding specificity to the *V. cholerae* O139 Bengal capsular polysaccharide, and the use of the same to detect and identify *V. cholerae* O139 Bengal infection.

In yet another embodiment, the above-described objects of the present invention have been met by a *V. cholerae* O139 Bengal capsular polysaccharide-protein conjugate that is capable of inducing said antibodies.

In still another embodiment, the above-described objects of the present invention have been met by a vaccine for treatment of *V. cholerae* O139 Bengal infection comprising a pharmaceutically effective amount of said capsular polysaccharide; and a pharmaceutically acceptable carrier or diluent.

DETAILED DESCRIPTION OF THE INVENTION

Figure 1:
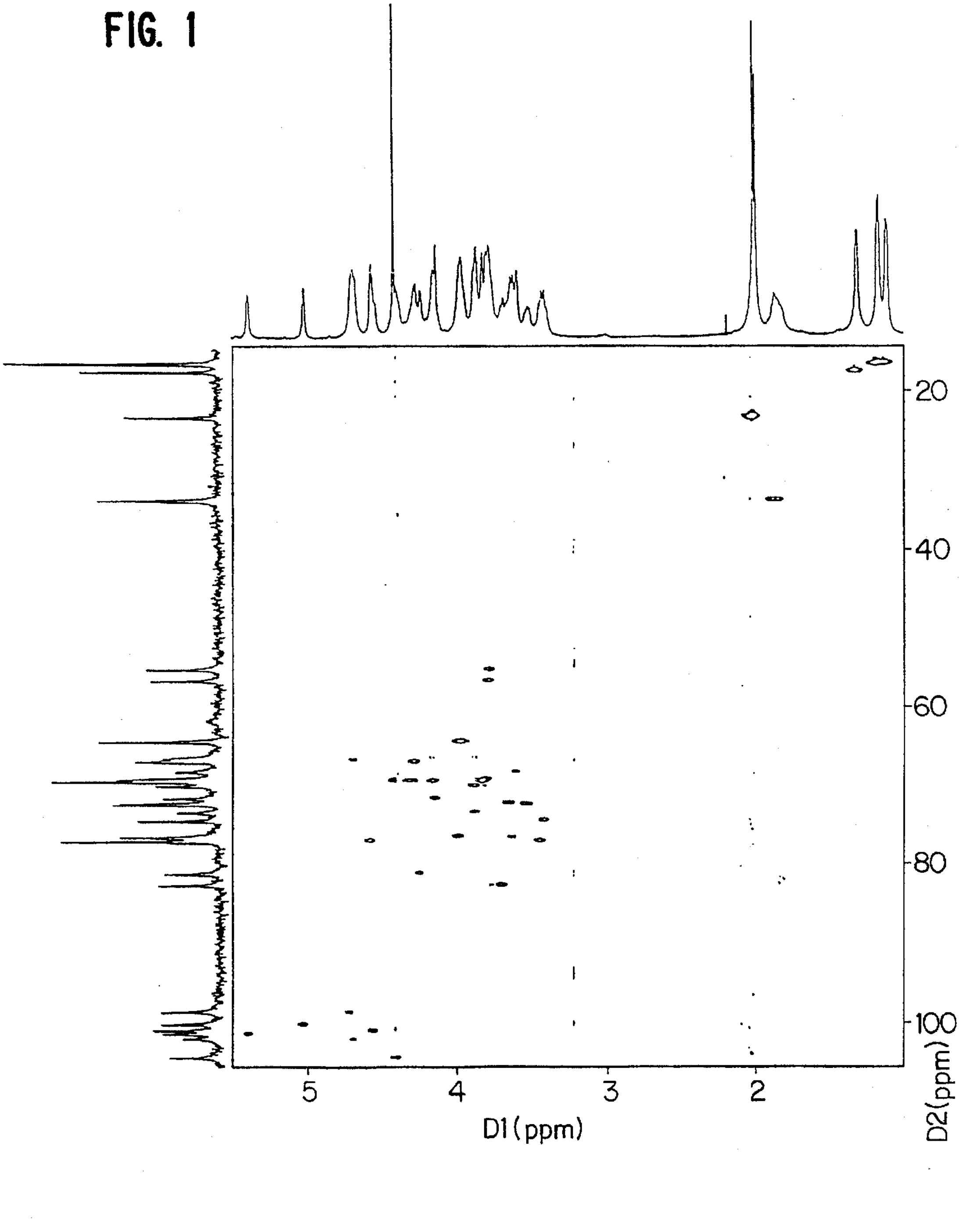
FIG. 1 shows the 2-dimensional $^1$H-detected heteronuclear $^{13}$C NMR spectrum (HMQC) at 500 MHz of the capsular polysaccharide purified from *V. cholerae* O139 Bengal strain AI1837.

In the present invention, a previously unknown capsular polysaccharide antigen, specific to *V. cholerae* O139 Bengal has been discovered, provided in substantially pure form and identified, inter alia, by its NMR profiles. As discussed above, it was unexpectedly discovered that the epidemic strain *V. cholerae* O139 Bengal expresses a unique capsular polysaccharide. Furthermore, it was unexpectedly discovered that humans exposed to live *V. cholerae* O139 Bengal induced high titers of antibodies which have binding specificity to this capsular polysaccharide. That is, during infection by O1 *V. cholerae*, the highest titers of antibody are raised to cholera toxin and lipopolysaccharide. Thus, it was unexpected that the titer of anticapsular antibodies was higher than that of the lipopolysaccharide (Levine et al, *Microbiol. Rev.,* 47:510–50 (1983)). In addition not all capsules are immunogenic (Finne et al, *Lancet*, ii:355–357 (1983)).

As used herein, the expression "substantially pure" means substantially free of contaminating proteins and lipids.

The particular *V. cholerae* O139 Bengal strain from which the capsular polysaccharide is purified is not critical to the present invention. Examples of such strains include strain AI1837, AI1838, AI1841, AI1842, AI1854, AI1855, AI4260, AI4450 and other O139 strains isolated from India, Bangladesh, and Thailand. These strains are well-known and readily available from the Centers of Disease Control and other laboratories (Albert et al, *Lancet*, 342:387–90 (1993); Jesudason et al, *Lancet*, 341:1090 (1993); and Chongsanguan et al, *Lancet*, 342:430–1 (1993)).

The capsular polysaccharide of this invention can be purified using the method of purification of the capsular polysaccharide from the non-O1 *V. cholerae* NRT36S strain, as described by Johnson et al, *Infect. Immun.*, 16:864–869 (1992).

Alternatively, the capsular polysaccharide can be purified by other established methods, such as precipitation with ethanol (Fattom at al, *Infect. Immun.*, 58:2367–2374 (1990) ), or precipitation with cetavalon (hexadecyl trimethyl ammonium bromide) (Cherniak et al, *Mol. Immunol.*, 17:1025–1032 (1980); and Gotshlich et al, *Monogr. Allergy*, 9:245–258 (1975)).

The substantially pure capsular polysaccharide of the present invention can be used to detect and identify *V. cholerae* O139 Bengal infection in a sample by well-known methods, and the particular method employed is not critical to the present invention. Examples of such methods include detection of precipitation of the purified capsular polysaccharide by a serum sample which contains antibodies to said capsular polysaccharide as a result of O139 Bengal infection; and detection of binding of antibodies to the substantially pure capsular polysaccharide in a standard enzyme linked immunosorbent assay (ELISA) using labeled antibodies (Harlow et al, Eds., *Antibodies: A Laboratory Manual*, Cold Spring Harbor Laboratory, Cold Spring Harbor, N.Y. (1990)).

The antibodies having binding specificity to the capsular polysaccharide of the present invention can be polyclonal or monoclonal antibodies. The polyclonal antibodies can be produced using the well-known techniques described by Harlow et al, supra. The monoclonal antibodies can be produced by hybridomas using the capsular polysaccharide as antigen, and the well-known technique described by Kohler et al, *Nature*, 256:495–497 (1975).

Protein carriers have been conjugated to polysaccharide antigens to improve their immunogenicity (Watson et al, *Infect. Immun.*, 60:4679–4686 (1992); and Wenget et al, *Lancet*, 338:395–398 (1991)). Thus, such protein carriers can also be employed to improve the immunogenicity of the capsular polysaccharide of the present invention, although the particular protein carrier employed is not critical to the present invention. Examples of such protein carriers include tetanus toxoid, cholera toxin, cholera toxin B subunit, bovine serum albumin, keyhole limpet cyanogen, ovalbumin, purified protein derivative of tuberculin, hemolysin, and synthetic peptides.

The method of conjugation of the capsular polysaccharide to the protein carrier employed is also not critical to the present invention. Examples of such conjugation methods include the use of 1-ethyl-3-(3-dimethylaminopropyl) carbodiimide (EDAC); and cyanogen bromide, as is well-known in the art (Watson et al, supra; Wenger et al, supra; and Harlow et al, supra).

The capsular polysaccharide-protein conjugate can be administered to an appropriate host in order to induce antibody formation using techniques well-known in the art (Harlow et al, supra; Devi et al, *Proc. Natl. Acad. Sci. USA*, 88:7175 (1991); and Fattom et al, *Infect. Immun.*, 58:2367–2374 (1990)). Examples of such hosts include mice, rabbits, goats, horses and sheep.

The amount of capsular polysaccharide-protein conjugate to be employed to induce antibodies is generally about 10 to 5000 μg/kg body weight, preferably about 250 to 500 μg/kg body weight.

The anticapsular antibodies of the present invention can be used to detect and identify *V. cholerae* O139 Bengal in a sample by well-known methods, and the particular method employed is not critical to the present invention. Examples of such methods include slide or tube agglutination or precipitation, ELISA, fluorescent antibody staining, immunoblots, or agar diffusion, with whole *V. cholerea*O139 Bengal cells or cell components using immune serum or purified antibodies (Harlow et al, supra; Devi et al, *Proc. Natl. Acad. Sci. USA*, 88:7175 (1991); and Fattom et al, *Infect. Immun.*, 58:2367–2374 (1990)).

In the context of the present invention, the term "sample" refers to an original clinical or environmental sample, or a cultured sample that is suspected to have *V. cholerae* O139 Bengal.

The unknown sample suspected of containing *V. cholerae* O139 Bengal may be a clinical sample, such as stool or blood from persons with diarrheal disease or cultures of bacteria grown from such. The unknown sample can also be derived from other animal sources, such as animal tissues, e.g., throat, skin, lung, muscle, bone, intestinal, liver, spleen and lymph node tissues; or animal fluids, such as urine, sputum, ear fluids, or a wound culture.

Additionally, environmental samples can be water samples, such as salt water, fresh water, and brackish water obtained from rivers, streams, lakes, marshes or other bodies of water, ground water, piped water, water stored in homes, filtration or purification plant effluents, soil, earth, and rock. Plants, crops or terrestrial or aquatic animals can also be sources, especially aquatic animals, such as shellfish, fish or marine mammals or water in which such animals are found.

Marine mammals can include whales, porpoises and dolphins. Shellfish can include, crabs, oysters, clams, mussels, lobsters, crayfish and the like. Terrestrial animals can include mammals, such as domestic animals, including livestock, and humans. Livestock can include cows, horses, pigs, goats and sheep. Domestic animals can include cats and dogs.

The unknown sample can also be obtained from DNA or RNA cloned and expressed using well-known methods, such as described in Maniatis et al, *Molecular Cloning: A Laboratory Manual*, Cold Spring Harbor Laboratory, Cold Spring Harbor, N.Y. (1982); and Gissman, *Cancer Surv.*, 3:161–181 (1984).

The capsular polysaccharide can also be used for active immunization against *V. cholerae* O139 Bengal infection. The amount of capsular polysaccharide to be administered such that it is useful as a vaccine against O139 Bengal infection will vary, inter alia, depending upon the species, age, weight and sex of the subject to be vaccinated. Generally the amount of polysaccharide-protein conjugate to be administered as a vaccine is about 10 to 5000 µg/kg body weight, preferably about 250 to 500 µg/kg body weight The capsular polysaccharide-protein conjugate can be administered via any suitable mode of administration, such as intramuscular, intravascular, subcutaneous, intradermal, oral or intranasal administration. The preferred mode of administration is intramuscular administration.

The capsular polysaccharide can be administered along with a pharmaceutically acceptable carrier or diluent. Examples of such pharmaceutically acceptable carriers include tetanus toxoid, cholera toxin B subunit. Examples of such protein carriers include tetanus toxoid, cholera toxin, cholera toxin B subunit, bovine serum albumin, keyhole limpet cyanogen, ovalbumin, purified protein derivative of tuberculin, and synthetic peptides. Examples of such pharmaceutically acceptable diluents include water, sodium bicarbonate buffer, or phosphate buffered saline.

The antibodies having binding specificity to the capsular polysaccharide can also be used for passive immunization against *V. cholerae* O139 Bengal infection. The amount of antibodies to be administered such that they are useful as a vaccine against O139 Bengal infection will vary, inter alia, depending upon the species, age, weight and sex of the subject to be vaccinated. Generally, the amount of such antibodies to be administered as a vaccine is about 0.001 to 10 gm/kg body weight, preferably about 0.1 to 1 gm/kg body weight.

The antibodies having binding specificity for the capsular polysaccharide can be administered via any suitable mode of administration, such as intramuscular, oral, intravascular, subcutaneous, or intranasal administration. The preferred mode of administration is intravascular administration.

The antibodies having binding specificity for the capsular polysaccharide can be administered along with a pharmaceutically acceptable carrier or diluent. Examples of such pharmaceutically acceptable carrier or diluents include water, phosphate buffered saline or sodium bicarbonate buffer.

The following examples are provided for illustrative purposes only and are in no way intended to limit the scope of the present invention.

EXAMPLE 1

Capsular Polysaccharide Production

*V. cholerae* O139 Bengal strains AI1837, AI1838, AI1841, AI1842, AI1854, AI1855, AI4260 and AI4450 were cultured on L-agar at 37° C. overnight, and were evaluated visually for opaque versus translucent colony morphology and phase shifting. All eight *V. cholerae* O139 Bengal strains had a moderately opaque colony morphology on initial streaks; translucent sectors and colonies appeared after subculturing. Similar changes in colony morphology were not seen when over one hundred O1 strains from clinical and environmental sources were examined.

In addition, two *V. cholerae* O139 Bengal strains (AI1852 and AI1841) were stained with polycationic ferritin, thin-sectioned and examined by electron microscopy as described by Johnson et al, supra. Both strains were found to be surrounded by a relatively thin electron dense capsule.

EXAMPLE 2

Capsular Polysaccharide Purification

The capsular polysaccharide of *V. cholerae* O139 Bengal was purified by first culturing cells from strain AI1837 at 37° C. for 18 hr on L-agar in petri dishes. The cells were then scraped off of the dishes, and suspended in 0.5 X phosphate buffered saline (PBS), shaken vigorously for 60 min at room temperature, and centrifuged at 16,000×g at 4° C. for 20 min to remove cell debris. The supernatant was then removed, and dialyzed against multiple changes of water for 24 hr. The supernatant was then 5 ultracentrifuged at 154,000×g at 20° C. for 16 hours, and the resulting supernatant was treated with 50 µg/ml of DNaseA and 100 µg/ml of RNaseA in the presence of 1.0 mM $MgCl_2$ at 37° C. for 1 hour, and thereafter treated with 250 µg/ml of pronase at 37° C. for 18 hours, and then subjected to phenol-chloroform extraction, dialysis against distilled water, and ultracentrifugation at 154,000 ×g at 20° C. for 2 hr, followed by lyophilization.

Samples were tested for protein contaminants using the Bio-Rad protein assay and Limulus amebocyte lysate assay for LPS (Sigma Chemical Co.). Samples contained no detectable protein and <0.01% LPS.

Carbohydrate concentration was determined as >99% by the standard phenol-sulfuric assay for sugars using a glucose standard curve (Dubois et al, *Anal. Chem.*, 3:350–356 (1950)).

EXAMPLE 3

Carbohydrate Analysis

The structure of the purified capsular polysaccharide obtained in Example 1 was determined by high performance anion exchange chromatography (HPAEC), and nuclear magnetic resonance (NMR) analysis.

More specifically, about 200 μg of the purified capsular polysaccharide obtained in Example 1 was subjected to hydrolysis in 4N HCl at 100° C. for 2 hr, and then analyzed on a HPAEC Carbopac PA1 column with a pulsed amperometric detector (PAD), as described by Reddy et al, *J. Bacteriol.*, 174:2620–2630 (1992); Reddy et al, *Anal. Biochem.*, 214:100–115 (1993); Lee et al, *Anal. Biochem.*, 189:278–2844 (1990); and Hardy at al, *Anal. Biochem.* 170:54–62 (1988).

In the resulting HPAEC chromatograph, peaks were detected whose retention times correspond to quinovosamine and glucosamine. Under conditions, i.e., 100 mM NaOH and 150 mM NaOAc, which are expected to detect acidic sugars, such as keto deoxy octanoate (KDO), sialic acid or uronic acids, no peaks were found. This latter result does not mean that the capsular polysaccharide is not necessarily acidic, since it could contain acidic groups such as pyruvate, sulfate or phosphate, which would not be detected by this method.

To confirm the HPAEC results, and to determine the sugar linkages, the capsular polysaccharide obtained in Example 1 was dissolved in $D_2O$ to a final concentration of about 10 mg/ml, and examined by NMR spectroscopy. $^1H$ and $^{13}C$ chemical shifts were determined, relative to internal sodium 4,4-dimethyl-4-silapentane-1, with acetone as the internal standard, on a General Electric GN-500 spectrometer, as described by Reddy et al (1992), supra. $^1H$ NMR spectra of the capsular polysaccharide in $D_2O$ showed an apparently homogeneous capsular polysaccharide sample with reasonably narrow lines (2 Hz).

Two dimensional $^1H$-detected heteronuclear $^{13}C$ spectrum (HMQC) spectra were recorded without sample spinning using the method of States et al, *J. Magn. Reson.*, 48:286–292 (1982). The results are shown in FIG. 1.

As shown in FIG. 1, the region of 4.4 to 5.5 ppm ($^1H$) and 98 to 105 ppm ($^{13}C$), which is characteristic of anomeric signals, shows six peaks, consistent with six residues in the repeating subunit. There are also two resonances in FIG. 1 in the region of 3.8 ppm ($^1H$) and 56 ppm ($^1C$). These resonances are characteristic of H2 and C2 of amino sugars. This is in agreement with the carbohydrate analysis in the HPAEC chromatography discussed above. In addition, in FIG. 1, there are three methyl doublets characteristic of 6-deoxy hexoses, and two methyl singlets characteristic of amide methyl functions of acetamido sugars (see also FIG. 3).

Homonuclear spin correlation using 2-dimensional double-quantum-filtered correlation spectroscopy (DQF-COSY) (Rance et al, *Biochem. Biophys. Res. Commun.*, 117:479 (1983)), and homonuclear Hartman-Hann spectroscopy (HOHAHA) (Bax et al, J. *Magn. Reson.*, 65:355–360 (1985)), has been used in order to identify the spin system of sugars (Abeygunawardana et al, *Advances in Biophysical Chemistry*, 3:199–249 (1993)). The multiplet shapes in these spectra indicate the stereochemistry, and thus the identity of the monosaccharides (Reddy et al (1993), supra).

Hence, DOF-COSY was carried out on the capsular polysaccharide obtained in Example 1 using the method of Rance et al, supra, and recorded at 500 MHz with standard pulse sequences to determine sugar linkages. The results are shown in FIG. 2.

In addition, HOHAHA was also carried out on the capsular polysaccharide obtained in Example 1 using the method of Bax et al, supra, and recorded at 500 MHz with standard pulse sequences to determine sugar linkages. The results are shown in FIG. 3.

Figure 2:
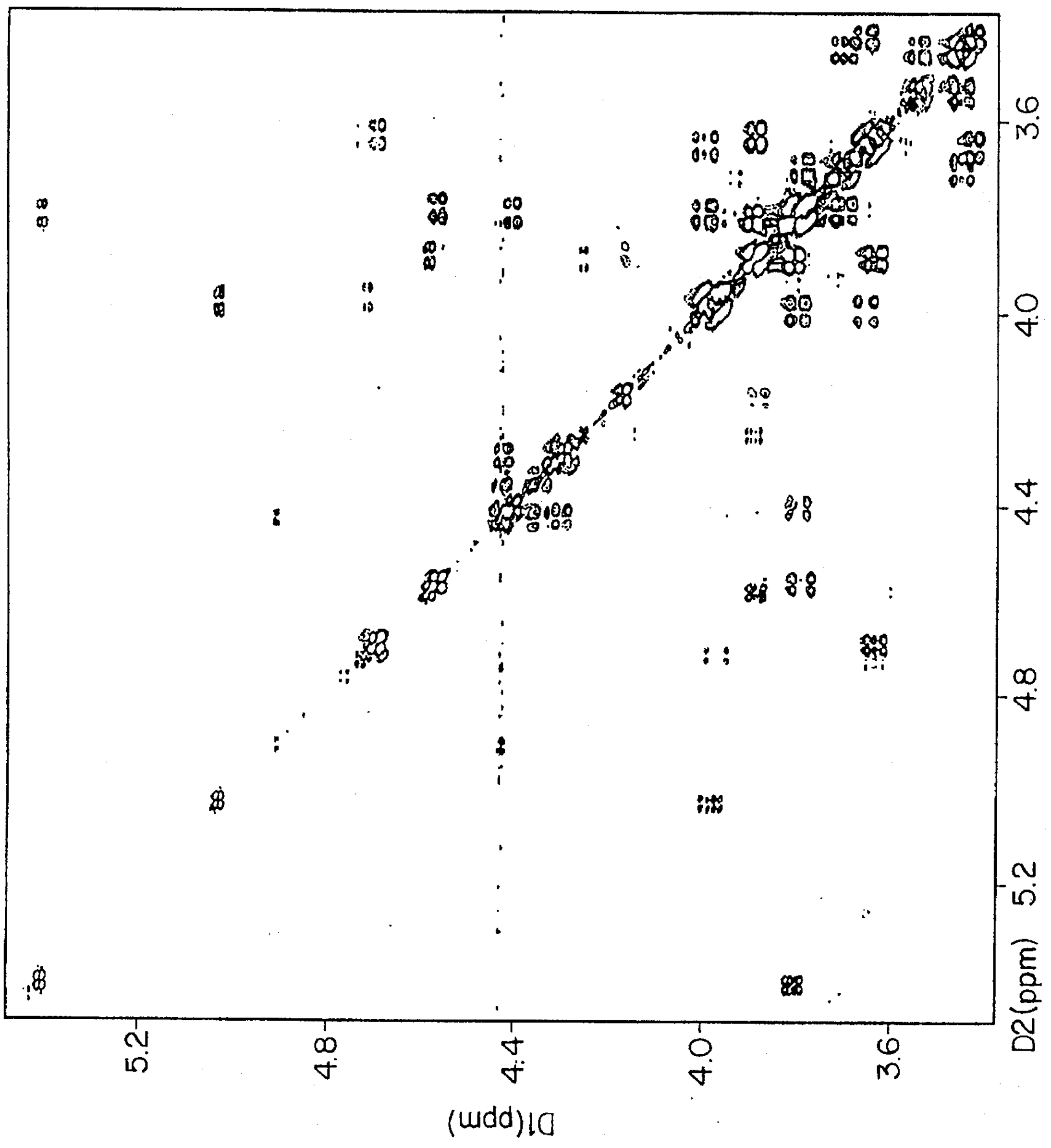
FIG. 2 shows the 2-dimensional $^1$H DQF-COSY spectrum at 500 MHz of the capsular polysaccharide purified from *V. cholerae* O139 Bengal AI1837.
Figure 3:
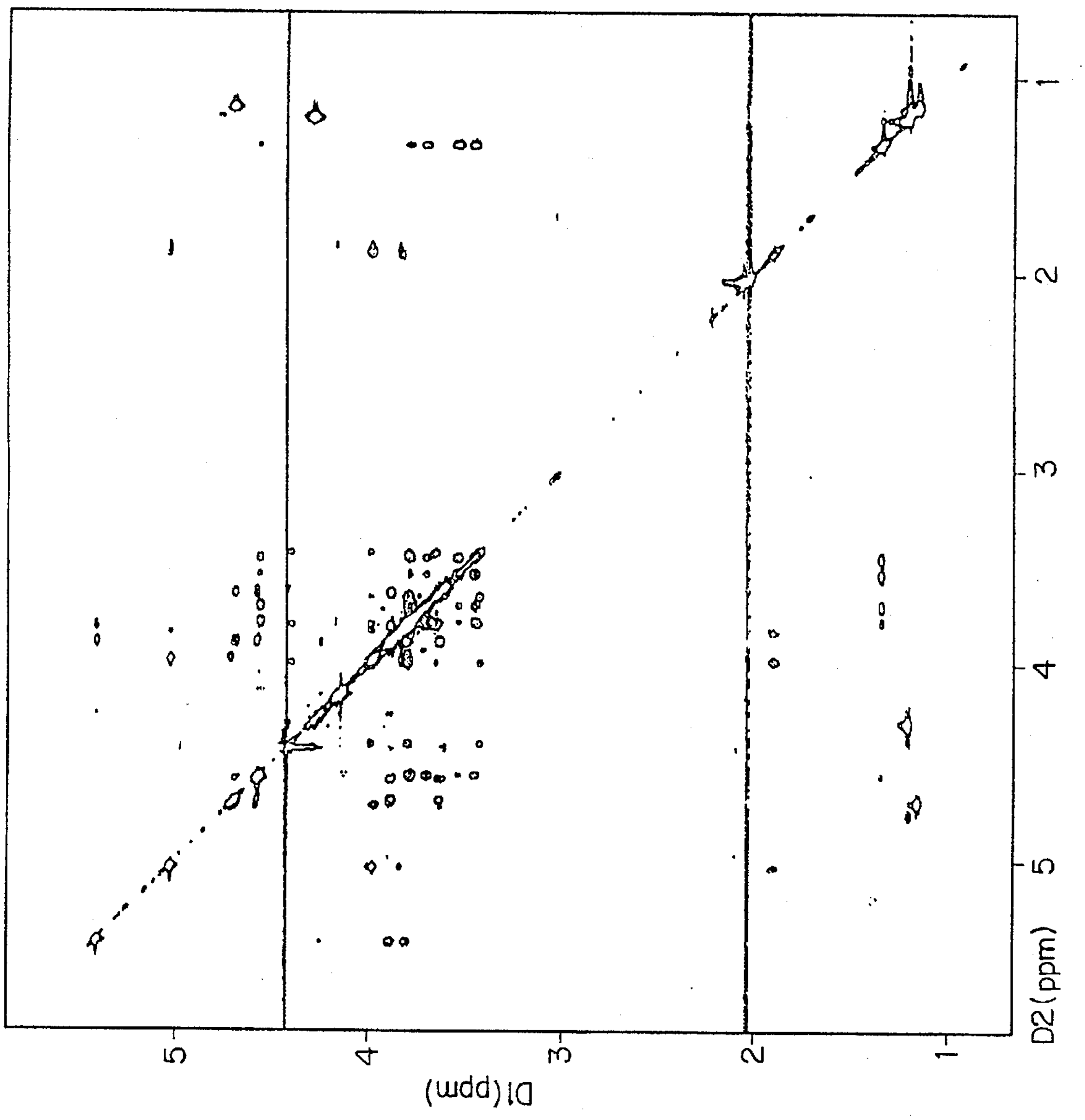
FIG. 3 show the 2-dimensional HOHAHA spectrum at 500 MHz of the capsular polysaccharide purified from *V. cholerae* strain O139 Bengal AI1837.

From the data in FIGS. 2 and 3, it is possible to identify the spin systems of one residue each of β-N-Acetyl quinovosamine and of β-N-Acetyl glucosamine. Two residues of the 3,6 di-deoxy sugar, abequose, have been identified in the assignment of the data of FIG. 2. A working hypothesis consistent with present data is that there are two additional spin systems associated with two other anomeric signals.

In summary, it was determined from the NMR analysis that the capsular polysaccharide contains more than 4 (probably six) sugars. Two have been identified as a quinovosamine (2-amino-2,6-dideoxyglucose) and a glucosamine; and there is no KDO (3-deoxy-D-manno-octulosonic acid) or uronic acids.

This structure is clearly distinct from the capsular polysaccharide of non-epidemic *V. cholerae* strains, and the capsular polysaccharide of other Vibrio species (Hayat et al, *J. Infect. Dis.*, 168:758–762 (1993)).

A literature search revealed no other capsular polysaccharide structure that matches this description. Thus, the polysaccharide can be clearly identified, i.e., distinguished from other capsular polysaccharide, based on its NMR and HPAEC profiles.

The molecular weight of the purified capsular polysaccharide was determined by size exclusion gel chromatography, and found to be between about 100,000 and 200,000.

EXAMPLE 4

Detection of Anticapsular Antibodies

Volunteers were infected with $10^4$ or $10^6$ CFU of *V. cholerae* O139 Bengal, and the production of human anticapsular antibodies was determined 10 days after inoculation by quantitation of antibody secreting cells (ASC) per $10^6$ freshly isolated peripheral blood mononuclear cells using the enzyme-linked immunosorbent assay described by Van de Verg et al, *Infect. Immun.*, 58:2002–2004 (1990); and Losonsky et al, *Infect. Immun.*, 61:729–733 (1993). Briefly peripheral blood mononuclear cells were separated by Ficoll-Hypaque density gradient centrifugation and added to antigen-coated microtiter plates. Plates were developed with IgA, IgG, or IgM specific goat-anti-human alkaline phosphatase conjugated antibody.

The volunteers were found to produce human anticapsular antibodies at both doses. Unexpectedly, at a low dose ($10^4$ CFU), human antibody response to the capsular polysaccharide was found to be several-fold higher then to the bacterial LPS. This was unexpected, as LPS is the cellular component, and LPS is the basis for the major of the antibody response to *V. cholerae* O1. These observations demonstrate that the capsule is expressed during natural infections of *V. cholerae* O139 Bengal, and therefore, that the capsular polysaccharide of the present invention can be used to assay serum for antibodies induced by exposure to *V. cholerae* O139 Bengal.

The titer of *V. cholerae* O139 Bengal in a serum sample from human or animal blood can be determined by testing dilutions of the serum in standard immunologic assays, such as precipitation of purified capsular polysaccharide in tubes or microtiter plates (Harlow et al, supra); or enzyme linked immunosorbent assay (ELISA) (Harlow et al, supra), in capsular polysaccharide coated microtiter plates or other support. In these assays, the capsular polysaccharide is bound directly to the microtiter plate, bound to modified plates, or modified to improve adherence. An example of a standard modification of microtiter plates is to coat the plates with charged polymers, such as poly-L-lysine (Giode et al *J. Infect. Dis.*, 39:52–59 (1979)). An example of a way to improve adherence of the capsular polysaccharide to the microtiter plate or other support is to mixed the capsular polysaccharide with methylated human serum albumin (Arakere et al, *Infect. Immun.*, 59:4349–4356 (1991)).

EXAMPLE 5

Capsular Polysaccharide-Protein Conjugates

Polysaccharide are generally poor antigens (Harlow et al, supra). Thus, to increase the antigenicity of the capsular polysaccharide obtained in Example 1, it was conjugated to tetanus toxoid (TT) (Conaught Laboratories Inc., Swiftwater, Pa.), as described by Devi et al, *Proc. Natl. Acad. Sci. USA*, 88:7175–7179 (1991).

More specifically, 5.0 mg/ml of purified capsular polysaccharide obtained in Example 1 in 0.2M NaCl was derivatized with 0.5M adipic acid dihydrazide (ADH) and 0.1M 1-ethyl-3-(3-dimethylaminopropyl) carbodiimide (EDAC) (pH 5.6) at room temperature for 3–4 hr. During the reaction, the pH was maintained with 0.25M HCl.

Thereafter, the reaction mixture was dialyzed extensively against 0.2M NaCl at 3°–8° C., for 2 days, and passed through Sepharose 4B-CL in 0.2M NaCl. The capsular polysaccharide-containing fractions were pooled, dialyzed against sterile pyrogen-free water, and freeze-dried. The content of adipic acid hydrazide (AH) was assayed as described by Schneerson et al, *J. Exp. Med.*, 152:361–276 (1980) to determine the efficiency of conjugation.

The resulting derivatized capsular polysaccharide was admixed with tetanus toxoid at equal concentrations of 7.5–20 mg/ml in 0.2M NaCl. The pH was adjusted between 6.1 and 7.0 with 0.1M HCl. Then, 0.1M EDAC was added, and the pH was maintained at 3°–8° C. for 3 hr. Next, the reaction mixture was dialyzed against 0.2M NaCl at 3°–8° C. for 16 hr, and then passed through Sepharose 4B-CL in 0.2M NaCl. The void volume fractions were pooled, assayed for protein, and stored in 0.01% thimerosal at 3°–8° C.

EXAMPLE 6

Introduction of Capsular Polysaccharide-Specific Antibodies

A host, such as mice, are injected subcutaneously three times, 15 days apart, with 5.6 μg of the capsular polysaccharide-tetanus toxoid conjugate obtained in Example 5 in PBS. Antibody titers are determined by ELISA (Harlow et al, supra) using capsular polysaccharide-coated Immulon IV (Dynatech) plates. Titers are determined using alkaline phosphatase-labeled goat anti-mouse IgG or IgM.

EXAMPLE 7

Identification and Detection of *V. cholerae* O139 Bengal

Identification of bacteria using an appropriate antibody is well-known to the art. For example, using the antibodies obtained in Example 6, slide agglutination tests are carried out using colonies from a pure culture of a suspect organism, or culture smears are stained using fluorescently-labelled antibodies (Harlow et al, supra).

While the invention has been described in detail, and with reference to specific embodiments thereof, it will be apparent to one of ordinary skill in the art that various changes and modifications can be made therein without departing from the spirit and scope thereof.

What is claimed is:

1. A substantially pure *V. cholerae* O139 Bengal capsular polysaccharide having Nuclear Magnetic Resonence (NMR) spectra as shown in FIGS. 1, 2 and 3.

2. A *V. cholerae* O139 Bengal capsular polysaccharide-protein conjugate that is capable of inducing antibodies having binding specificity to the capsular polysaccharide of claim 1.

3. The *V. cholerae* O139 Bengal capsular polysaccharide-protein conjugate of claim 2, wherein said protein is selected from the group consisting of tetanus toxoid, cholera toxin, cholera toxin B subunit, bovine serum albumin, keyhole limpet cyanogen, ovalbumin and hemolysin.

4. A vaccine for treatment of *V. cholerae* O139 Bengal infection comprising a pharmaceutically effective amount of the conjugate of claim 2; and a pharmaceutically acceptable carrier or diluent.

* * * * *

UNITED STATES PATENT AND TRADEMARK OFFICE
CERTIFICATE OF CORRECTION

PATENT NO. : 5,653,986 
DATED : August 5, 1997
INVENTOR(S) : J. Glenn Morris Jr., Judith A. Johnson and Allen Bush It is certified that error appears in the above-identified patent and that said Letters Patent is hereby corrected as shown below:

<u>Column 1,</u>
Line 9, add the following text:
-- The development of the present invention was also supported by a grant from National Institutes of Health, NIH Grant No. R01 Al 28856. The U.S. government has certain rights in this invention. --

Signed and Sealed this

Twenty-third Day of July, 2002

Attest:

JAMES E. ROGAN

*Attesting Officer* *Director of the United States Patent and Trademark Office*